(12) United States Patent
Bizar

(10) Patent No.: US 6,633,820 B2
(45) Date of Patent: Oct. 14, 2003

(54) SYSTEM FOR ASSESSING METAL DETERIORATION ON MARITIME VESSELS

(75) Inventor: Richard S. Bizar, Oakton, VA (US)

(73) Assignee: Xybernaut Corporation, Fairfax, VA (US)

(*) Notice: Subject to any disclaimer, the term of this patent is extended or adjusted under 35 U.S.C. 154(b) by 166 days.

(21) Appl. No.: 09/727,061

(22) Filed: Nov. 30, 2000

(65) Prior Publication Data

US 2002/0065612 A1 May 30, 2002

(51) Int. Cl.[7] .................................................. G01B 5/28
(52) U.S. Cl. ........................................................ 702/38
(58) Field of Search ................... 702/38, 83; 364/512, 364/507, 551; 73/620; 128/731; 600/545; 137/551; 378/98.2

(56) References Cited

U.S. PATENT DOCUMENTS

| | | | | |
|---|---|---|---|---|
| 4,800,895 A | * | 1/1989 | Moberg et al. | 128/731 |
| 4,998,208 A | * | 3/1991 | Buhrow et al. | 364/512 |
| 5,476,010 A | * | 12/1995 | Fleming et al. | 73/620 |
| 5,930,330 A | * | 7/1999 | Wolfe et al. | 378/98.2 |
| 6,094,623 A | * | 7/2000 | Mintchev et al. | 702/85 |
| 6,097,981 A | * | 8/2000 | Freer | 600/545 |

* cited by examiner

Primary Examiner—John Barlow
Assistant Examiner—Tung Lau
(74) Attorney, Agent, or Firm—James J. Ralabate

(57) ABSTRACT

This invention involves an apparatus for on-site testing and inspecting of metal structures and their deterioration. The NDT and hands free computer are both worn by the inspector to give him or her immediate results of the test.

27 Claims, 1 Drawing Sheet

SYSTEM FOR ASSESSING METAL DETERIORATION ON MARITIME VESSELS

This invention relates to a system and apparatus for inspecting and assessing metal deterioration on ships and, more specifically, a novel inspection system using wearable computers.

BACKGROUND TO THE INVENTION

In the marine industry ships are inspected and gauged. This activity takes place at specified intervals and at predetermined locations. In particular, chemical and oil tankers and bulk carriers are subject to metal deterioration, because of corrosion, at a faster rate than other types of ships. Significant metal loss places the vessel at risk of severe casualty and/or loss.

Current inspection/gauging practice has the inspector obtaining data while on the vessel, but then information must be transferred from a hand-held device to a more powerful computer for download, comparison with a stored database and analysis. This activity takes time and the vessel, in most cases, is underway—engaged in normal operations when actual hull condition is determined. Obviously, if there is a significant problem discovered as a result of analysis, then the vessel is at risk. The overwhelming reaction to discovery of the problem is to let the vessel continue its operation. This decision can be fatal, as in the case of vessels that have been lost in heavy weather because of deteriorated hull strength.

It is important in international and other shipping, to ensure safe vessels are used at sea, and procedures are set up to minimize dangerous conditions caused by ship corrosion or failures. Since the sea is highly corrosive, the steel thickness of vessels is of critical importance to safe operation.

There are several known measurement methods of determining steel thickness; some involve destructive testing while others use non-destructive testing methods, hereinafter "NDT". Some of these methods are disclosed in a brochure entitled "Resonance Thickness Measurement" published by Det Norske Veritas, Region Norway/RN010, Veritasveien 1, N-1322 Hovik Norway, hereinafter "Veritas".

Merchant ships are gauged by radiographic (x-ray) or ultrasonically to asses structural condition. A leading maker of this type of ultrasonic tester is Krautkramer, whose address is 50 Industrial Park Road, Lewistown, Pa. 17044. Results pend comparison with a known database to determine metal deterioration. This may be determination on hull and internal members of the ship structure. If the deterioration is greater than preset limits, corrective action is required. The time to accomplish this and implement a repair decision may be days or even weeks during which time the ship sails with possible dangerous defects. Not only does the physical inspection take a substantial time, but also taking these readings to an off-site computer to compare against set standards also takes considerable time. A known database is usually set in the computer to be used and time available on this computer and the physical distance between the computer and the inspection site have extended the corrective period to an unacceptable time. A system for immediate and instant on-site inspection and analysis would be extremely important for this industry.

When the term "metal diagnostics" is used throughout this disclosure and claims it is intended to include all of the metal inspection methods and apparatus disclosed in the above-noted Veritas article in addition to other suitable inspection systems. The most often used NDT devices (non-destructive testing devices) in this metal inspection are ultrasonics or radiographic means, including those of Veritas. As stated in Veritas:

What is Resonance Thickness Measurement (RTM)?
 1. The resonance method is a well-known principle, but not commercialized until recently due to lack of transmitter and computing technology. In contradiction to traditional ultrasonic inspection, the resonance method is capable of processing accurate thickness on heavily corroded surfaces.

What is the RTM Probe?
 2. A new tool for reliable and more efficient thickness measurements on corroded steel surfaces, based upon resonance technology.
 3. Present measurement range 3–30 mm, accuracy +/−0.1 mm.
 4. The tool may be used in both air and fluid. When used in air, there is no need for couplant gel.
 5. The mean ('strength thickness') of a 'footprint' of approx. 60 mm diameter is measured.
 6. Automatic data logging of 50,000 readings with optional 20 character numeric tag.
 7. The RTM method cannot be used for crack detection or lamellar check.
 8. Removal of scaling (corrosion products) or coating is not required.

What is the Wet Surface Hull Scanner (WSHS)?
 9. The WSHS consists of several RTM sensors mounted on a carrier (ROV) for scanning of a vessel's wet surface.
 10. Due to the advanced processing, scanning at a speed of up to 1 m/s is offered, thus ensuring more cost effective inspection.
 11. When combined with the specially developed high accuracy navigation system SWAPS, data from the scanned area is digitally dumped directly into a 3D product model, e.g. DNV Nauticus database. All data are processed on-line, enabling presentation of report results upon completed scanning.

Technical Summary:
ROV unit weight: approx. 50 kg
Total system weight: 150 kg
Dimensions: 1.06 m×1.25 m×0.38 m
Coverage: 100% of wet surface at detection speed of 1 $m^2$/s
Survey extent: 100% of scanned area
Measurement accuracy: +/−0.1 mm
Measurement output: Mean strength thickness, independent of back wall pitting Since inspection of ships requires climbing on or around a ship and manually maneuvering measuring devices, it is highly desirable to provide a hands-free system where the user is free to use his hands to conduct the desired analysis. Heretofore, nothing exists that allows this type of hands-free diagnostics.

SUMMARY OF THE INVENTION

It is therefore an object of this invention to provide a hands-free diagnostics system for NDT methods of checking metal, devoid of the above-noted disadvantages.

Another object of this invention is to provide a hands-free system and apparatus for on-site determination of metal deterioration.

Yet another object of this invention is to provide a more time efficient system for determination of metal deterioration on ships or other metal containing structures.

Still a further object of this invention is to provide an economical and efficient method of improving on the prior used metal deterioration determinations.

These and other objects of this invention are accomplished by a system and apparatus wherein the metal diagnostics equipment is worn by the user together with a hands-free activated wearable computer. By combining NDT metal diagnostics equipment with wearable PCs, the information becomes readily available at the site for decision makers and thus immediate corrective action can be taken. By combining an ultrasonic testing device with a wearable computer, all data manipulation can take place on board the vessel at the time of the inspection. Having this data immediately available reduces the probability of disaster to almost zero. Owners/operators can make timely and necessary repairs, so the vessel can safely resume its normal operations. As a further benefit of combining technologies, vessel crews can inspect and monitor hull conditions on a regular basis while underway, allowing for more careful planning and scheduling of repairs and/or drydockings.

An ultrasonic tester (or metal diagnostics) that can be attached to a wearable PC is that tester manufactured by Krautkramer whose address is 50 Industrial Park Road, Lewistown, Pa. 17044. As readings are obtained by the inspector, they are input directly into the full function wearable PC and compared with a known database. This provides instant results available on site so that decisions can be made before the ship can sail with a dangerous defect. This prevents casualties and saves lives and money from vessel and cargo loss. As noted earlier, the testing device or metal diagnostics can be ultrasonic or radiographic. The testing program is loaded directly into the wearable computer so that all that is needed is a test transducer coming directly from the wearable PC. The wearable PC will have a dedicated program installed, along with the baseline data from the ship being tested. As the readings are entered, the program will manipulate the data by comparing the new entries with the baseline data by using formulas, etc. and the results will be immediately available for decision-makers. This methodology can be used on pipelines (oil/gas/water), as well as on structural steel during maintenance inspections of any kind. The process of having Wearable Computer power at the site of testing allows immediate information to be available to be acted on. This could be pertinent during the construction stage in the building industry, as well as highways and bridges where weld defects must be found by NDT. This methodology provides immediate data manipulation and results for on site decision making. Note: The current testing devices do not have sufficient memory or power to handle current readings and manipulate large existing databases and comparison programs. Additionally, hands must be free to position the tester to the surface being tested. You cannot hold a laptop and test and a palm cannot handle the full process from testing to results. There is also a degree of safety added to the inspection process when hands are free to climb, hold on and take readings. The advantages of the system of this invention include:

1. Accuracy of readings and results.
2. Permanent electronic record of results, including date stamps of each gauge point.
3. Immediate results for analysis through computer processing of information at site.
4. Safety of inspectors performing the gauging due to hands-free capabilities.
5. Efficiency—Information obtained much faster than in the past and fewer resources needed to accomplish the full inspection. Less cost because less inspectors for a shorter time.
6. Continuous monitoring—the vessel operator can continually monitor the hull and scantling condition while the vessel is underway. This allows early detection of problems and therefore early planning and scheduling of repairs as needed. This saves downtime due to unplanned but required repairs. Cargoes can be lost because the vessel is not ready to sail and unscheduled downtime is costly.
7. Lower insurance rates—When Classification Societies and Insurers accept this continuous monitoring and analysis of a vessels hull condition, they will reward those vessels that maintain a good record and demonstrate the hull strength through electronic documentation of their condition over time.
8. Reduced risk of Casualty—Early analysis at site reduces the risk of casualty due to hull defects if vessel sails before the hull condition is known. This is the current situation as vessels sail while their inspection results are being analyzed ashore.
9. Saves potential liability and costs of a marine casualty—Preventing a casualty by anticipating problems, analyzing, and correcting them. The costs of a marine casualty are enormous. Loss of the vessel, cargo and human life is always possible when a vessel is in distress at sea. Damage to the environment when a vessel spills oil or chemicals results in severe consequences and astronomical costs and damages the reputation of the spiller.
10. Ease of use—The combination tester is user friendly. There will be a short learning period required of the operator. Training will be provided.
11. Multifunction capabilities—The combination device can be used for thickness gauging of hulls and internals and can also be used on pipe and pressure vessels. It can, with additional training, be used for flaw detection of welds in any metal.

The compact self-contained wearable computers used with the metal diagnostic device of this invention are the wearable computers disclosed in U.S. Pat. No. 5,305,244 (Newman et al I) and U.S. Pat. No. 5,844,824. In U.S. Pat. No. 5,305,244 a compact, self-contained portable computing apparatus is provided which is completely supported by a user for hands-free retrieval and display of information for the user. The computing apparatus includes a voice-recognition module, in communication with a processor, for receiving audio commands from the user, for converting the received audio commands into electrical signals, for recognizing the converted electrical signals and for sending the recognized electrical signals to the processor for processing, the voice-recognition module being supported by the user. The computing apparatus further includes a display in communication with the processor for receiving information from the processor and for displaying the received information for the user, the display being supported by the user whereby the user may operate the computing apparatus to display information in a hands-free manner utilizing only audio commands.

In U.S. Pat. No. 5,844,824 a wearable computer is directed to a compact, self-contained portable computing apparatus at least part of which is completely supported by a user for hands-free retrieval and display of information for the user. The computing apparatus includes a housing which may or may not have securing means for removably securing the housing to a user for support by the user. Alternatively, the housing may be located in a remote location not attached to the user and apart from the other components. The housing further includes storage means for storing previously entered information, and processor means, communicating with the storage means, for receiving, retrieving and processing information and user commands in accordance with a stored program. Since large databases of ETMs and IETMs will be accessed by the mobile self-contained computing apparatus, a means of easily interfacing storage means containing the databases is required. The housing of the computing apparatus includes an access port whereby various storage means containing data can be interfaced and communication established. Access and transfer of data between the storage means and the computing apparatus can be accomplished entirely under control of various hands-free activation means described in this application. The access port allows direct electrical attachment of the storage means; however, other wired and wireless connections are also used. The computing apparatus also includes eye tracking, brain actuation means, transducer and converter means with or without audio transducer and converter means in communication with the processor means, for receiving commands from the user, for converting the received commands into electrical signals, for recognizing the converted electrical signals, and for sending the recognized electrical signals to the processor means. The transducer and converter means may or may not be supported by the user. The computing apparatus further includes display means in communication with the processor means for receiving information from the processor means and for displaying the received information for the user, the display means being supported by the user whereby the user may operate the computing apparatus to display information in a hands-free manner utilizing only brain activation or eye tracking with or without audio commands.

In addition to the voice activation means used in Newman et al I as noted earlier, these two other above-noted activation means have been contemplated by the present invention, i.e. eye-tracking and brain-activation means (EEG). Using the same general system described in Newman et al I, voice activation may be fully or partially replaced by or used with either eye-tracking means and/or by Brain Actuated technology means. In some situations, any combination of voice-activation means, eye-tracking activation means and brain-actuation means may be desirable in a Newman et al I type portable, hands-free computer system. In combination with the above activation means some computing environments may utilize head and arm tracking means, for example, such an environment could be a virtual reality application. Both the disclosures of U.S. Pat. No. 5,305,244 and U.S. Pat. No. 5,844,824 are incorporated by reference into the present disclosure. As stated in both U.S. Pat. Nos. 5,305,244 and 5,844,824, the wearable PC can have communicating means as part of the structure, said communicating means are selected from the group consisting of portable phones, cellular telephones, hard line telephones, radios, infra red transceivers, two-way radio means and mixtures thereof. Ports can be located in the hands-free computer for connection to peripherals, such as cameras, printers, PCMCIA cards or other suitable peripherals.

The foregoing and additional objects and advantages of the invention together with the structure characteristics thereof, which is only briefly summarized in the foregoing passages, becomes more apparent to those skilled in the art upon reading the detailed description and preferred embodiments, which follow in this specification, taken together with the illustration thereof presented in the representative accompanying drawings.

DETAILED DESCRIPTION OF THE INVENTION AND PREFERRED EMBODIMENTS

Figure 1:
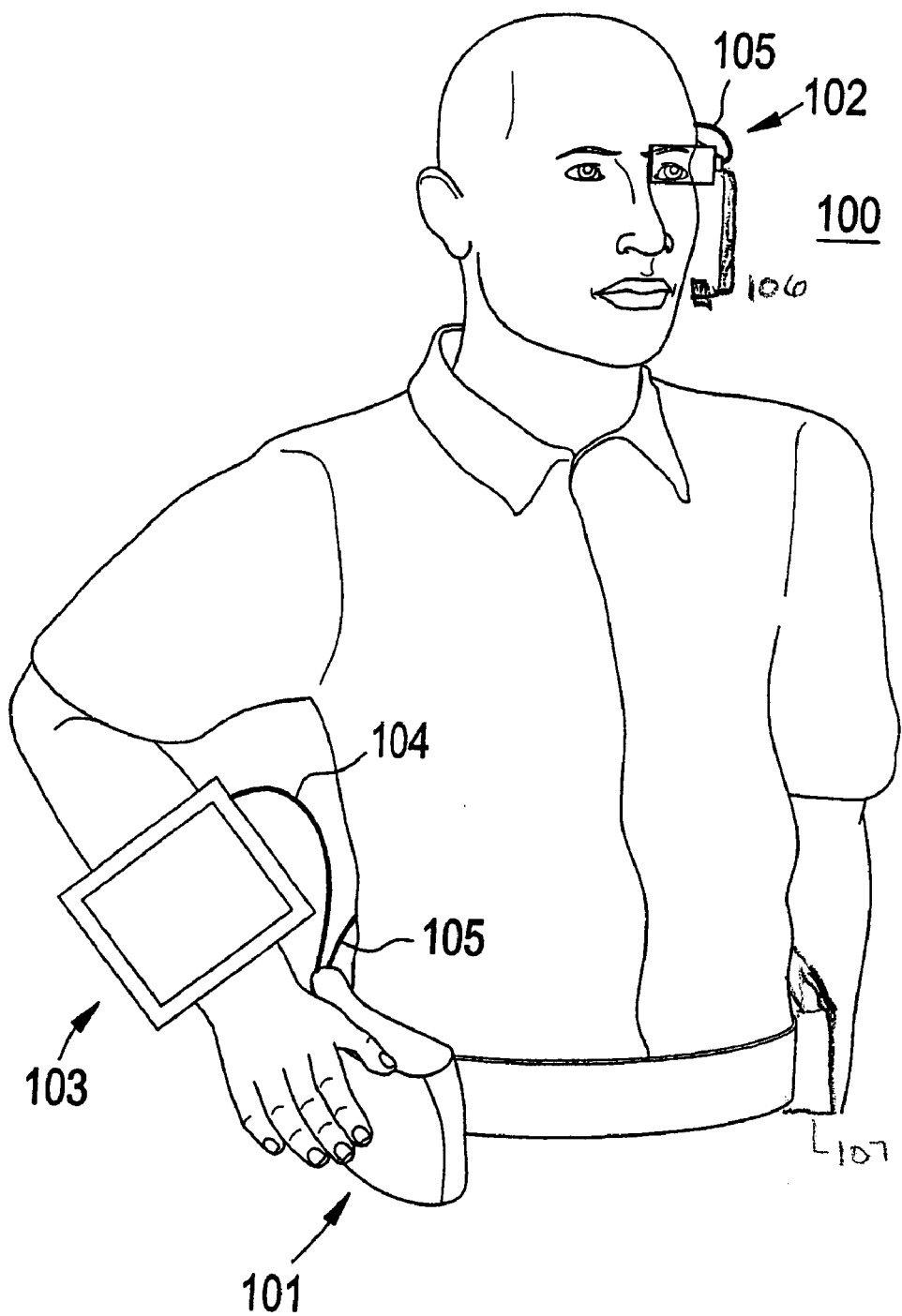
FIG. 1 illustrates a preferred embodiment of the present invention.

Discussion of the invention will now be made with specific references to the drawing figures. FIG. 1 illustrates a preferred embodiment of the instant invention illustrated generally by reference number 100. A user is shown with a user-supported computer 101 and head-mounted display 102 electrically connected via cable 105. The cable may provide power to the head-mounted display as well as provide a data connection to the computer. Alternatively, the head-mounted display may have its own power source and be wirelessly connected to the computer using a conventional wireless protocol such as IEEE 802.11x, Bluetooth, or other suitable protocol. The illustration shows a head-mounted display; however, other types of user-supported displays 103 may be used alone or together with other displays such as neck-hung displays, flat panel displays, and wrist-mounted displays. The computer maybe user-supported or a remote general-purpose that is capable of communicating wirelessly with the head-mounted display. The head-mounted display includes a microphone 103 for speech activation. The diagnostic probe 107 may be attached to the user such as clipped on the user's belt as illustrated when not in use. The probe 107 can be connected to the computer 101 using any suitable interface, such as serial, parallel, proprietary, or other suitable interface.

The preferred and optimumly preferred embodiments of the present invention have been described herein and shown in the accompanying drawings to illustrate the underlying principles of the invention, but it is to be understood that numerous modifications and ramifications may be made without departing from the spirit and scope of this invention.

What is claimed is:

1. An apparatus for on-site testing and analysis of deterioration of metal structure which comprises a wearable NDT metal diagnostic device used with a wearable hands-free computer, said wearable hands free computer comprising a display in connection thereto and having hands-free activation means selected from the group consisting of audio activation means, eye-tracking activation means, electroencephalography activation means and mixtures thereof, said apparatus comprising means for mounting both said display and said hands-free computer on the user such that the display is carried hands-free in view of the user, and wherein said computer is enabled to process data transmitted from said diagnostic device and analyze said data in conjunction with a database stored in a memory in said computer wherein said database contains information including historic and baseline data of the item being inspected, and wherein said data gathering and analysis is performed at the location of inspection.

2. The apparatus of claim 1 wherein said NDT metal diagnostic device is selected from the group consisting of ultrasonic means, radiographic means, resonance thickness measurement means and mixtures thereof.

3. The apparatus of claim 1 wherein said NDT metal diagnostic device is ultrasonic.

4. The apparatus of claim 1 wherein said NDT metal diagnostic device is radiographic.

5. The apparatus of claim 1 wherein an ultrasonic testing program or a radiographic testing program is loaded directly into said wearable hands-free computer.

6. The apparatus of claim 1 wherein said wearable hands-free computer has a port for connection to a printer.

7. The apparatus of claim 1 wherein said wearable hands-free computer has a port for connection to a camera.

8. The apparatus of claim 1 wherein said apparatus comprises communication means selected from the group consisting of portable phones, cell phones, hard wire phones, radios, infra-red transceivers, two-way radios and mixtures thereof.

9. The apparatus of claim 1 wherein said wearable hands-free computer, said NDT metal diagnostics device and said display are combined into a single housing worn by the user in a hands-free manner.

10. An system for on-site diagnostics and analysis of a metal structure of a ship which comprises a wearable NDT metal diagnostic device which is used in a hands-free manner, and a wearable hands-free computer in electrical connection to said NDT metal diagnostic device, said system optionally comprising a display device which is in electrical connection to said NDT metal diagnostic device and said wearable hands-free computer, said wearable hands-free computer having activation means selected from the group consisting of audio activation means, eye-tracking activation means, electroencephalography activation means and mixtures thereof, and wherein said computer is enabled to process data transmitted from said diagnostic device and analyze said data in conjunction with a database stored in a memory in said computer wherein said database contains information including historic and baseline data of the item being inspected, and wherein said data gathering and analysis is performed at the location of inspection.

11. The system of claim 10 wherein said NDT metal diagnostic device is selected from the group consisting of ultrasonic means, radiographic means, resonance thickness measurement means and mixtures thereof.

12. The system of claim 10 wherein said NDT metal diagnostic device is ultrasonic.

13. The system of claim 10 wherein said NDT metal diagnostic device is radiographic.

14. The system of claim 10 wherein an ultrasonic testing program or a radiographic testing program is loaded directly into said wearable hands-free computer.

15. The system of claim 10 wherein said wearable hands-free computer has a port for connection to a printer.

16. The system of claim 10 wherein said wearable hands-free computer has a port for connection to a camera.

17. The system of claim 10 wherein said apparatus comprises communication means selected from the group consisting of portable phones, cell phones, hard wire phones, radios, infra-red transceivers, two-way radios and mixtures thereof.

18. The system of claim 10 wherein said wearable hands-free computer, said NDT metal diagnostics device and said display are combined into a single housing worn by the user in a hands-free manner.

19. A method for on-site testing of deterioration of a metal structure which comprises providing a wearable NDT metal diagnostic device to be used with a wearable hands-free computer providing said wearable hands-free computer with a display in electrical connection thereto providing in said hands-free computer hands-free activation means selected from the group consisting of audio activation means, eye tracking activation means, electroencephalography activation means and mixtures thereof, providing means for mounting both said display and said hands-free computer on the user such that the display is carried hands-free in view of the user, and providing means such that said computer is enabled to process data transmitted from said diagnostic device and analyzing said data in conjunction with a database stored in a memory in said computer wherein said database contains information including historic and baseline data of the item being inspected, and wherein said data gathering and analysis is performed at the location of inspection.

20. The method of claim 19 wherein said NDT metal diagnostic device is selected from the group consisting of ultrasonic means, radiographic means, resonance thickness measurement means and mixtures thereof.

21. The method of claim 19 wherein said NDT metal diagnostic device is ultrasonic.

22. The method of claim 19 wherein said NDT metal diagnostic device is radiographic.

23. The method of claim 19 wherein an ultrasonic testing program or a radiographic testing program is loaded directly into said wearable hands-free computer.

24. The method of claim 19 wherein said wearable hands-free computer has a port for connection to a printer.

25. The method of claim 19 wherein said wearable hands-free computer has a port for connection to a camera.

26. The method of claim 19 wherein said apparatus comprises communication means selected from the group consisting of portable phones, cell phones, hard wire phones, radios, infra-red transceivers, two-way radios and mixtures thereof.

27. The method of claim 19 wherein said wearable hands-free computer, said NDT metal diagnostics device and said display are combined into a single housing worn by the user in a hands-free manner.

* * * * *